US012699898B2

(12) United States Patent
Nagao

(10) Patent No.: US 12,699,898 B2
(45) Date of Patent: Aug. 4, 2026

(54) METHOD, INFORMATION PROCESSING DEVICE, AND RECORDING MEDIUM STORING INSTRUCTIONS FOR PREDICTION

(71) Applicant: DIC Corporation, Tokyo (JP)

(72) Inventor: Atsushi Nagao, Osaka (JP)

(73) Assignee: DIC Corporation, Tokyo (JP)

( * ) Notice: Subject to any disclaimer, the term of this patent is extended or adjusted under 35 U.S.C. 154(b) by 477 days.

(21) Appl. No.: 18/561,573

(22) PCT Filed: May 22, 2023

(86) PCT No.: PCT/JP2023/019011
§ 371 (c)(1),
(2) Date: Nov. 16, 2023

(87) PCT Pub. No.: WO2024/142427
PCT Pub. Date: Jul. 4, 2024

(65) Prior Publication Data
US 2025/0086453 A1 Mar. 13, 2025

(30) Foreign Application Priority Data
Dec. 28, 2022 (JP) ................................. 2022-212704

(51) Int. Cl.
*G06N 3/08* (2023.01)
*G16C 20/10* (2019.01)
*G16C 20/70* (2019.01)

(52) U.S. Cl.
CPC ............... *G06N 3/08* (2013.01); *G16C 20/10* (2019.02); *G16C 20/70* (2019.02)

(58) Field of Classification Search
None
See application file for complete search history.

(56) References Cited

U.S. PATENT DOCUMENTS

2003/0073787 A1 4/2003 Stephens et al.
2022/0101142 A1* 3/2022 Tsai ....................... G06N 3/048
(Continued)

FOREIGN PATENT DOCUMENTS

CN 102680646 A 9/2012
CN 113222278 A 8/2021
WO 2003026791 A1 4/2003

OTHER PUBLICATIONS

Haripriyan Uthayakumar et al., "Growth of MWCNTs from Azadirachta indica oil for optimization of chromium(VI) removal efficiency using machine learning approach"; Environmental Science and Pollution Research, Springer Berlin Heidelberg, Berlin/Heidelberg, vol. 29, No. 23 pp. 34841-34860; Jan. 18, 2022 (20 pages).

(Continued)

*Primary Examiner* — Richard L Bowen
(74) *Attorney, Agent, or Firm* — Osha Bergman Watanabe & Burton LLP

(57) ABSTRACT

A method for prediction executed by an information processing device includes: training a neural network model based on actual data on a prediction target; and predicting an objective factor related to the prediction target based on explanatory factors related to the prediction target by the neural network model. The neural network model includes an input layer, an intermediate layer, and an output layer, and a coefficient of an activation function of the intermediate layer is larger than a coefficient of an activation function of the output layer.

10 Claims, 7 Drawing Sheets

(56) References Cited

U.S. PATENT DOCUMENTS

| | | | |
|---|---|---|---|
| 2023/0048253 A1* | 2/2023 | Ohmae | ............... G01R 31/392 |
| 2025/0103932 A1* | 3/2025 | Prati | ..................... G06N 10/20 |

OTHER PUBLICATIONS

Surendra D. Barewar et al., "Experimental investigation of thermal conductivity and its ANN modeling for glycol-based Ag/ZnO hybrid nanofluids with low concentration"; Journal of Thermal Analysis and Calorimetry, Kluwer, Dordrecht, NL, vol. 139, No. 3, pp. 1779-1790; Jul. 30, 2019 (12 pages).

* cited by examiner

METHOD, INFORMATION PROCESSING DEVICE, AND RECORDING MEDIUM STORING INSTRUCTIONS FOR PREDICTION

CROSS-REFERENCE TO RELATED APPLICATIONS

The present application claims priority from Japanese Patent Application No. 2022-212704, filed on Dec. 28, 2022, the contents of which are incorporated herein by reference.

BACKGROUND

Technical Field

The present disclosure relates to a method for prediction, an information processing device, and a recording medium storing instructions.

Description of Related Art

Conventionally, methods for performing prediction related to physical and chemical phenomena such as chemical reactions have been developed (for example, PTL 1).

PATENT LITERATURE

PTL 1: WO 2003/026791

The technique described in PTL 1 has described the use of modeling techniques such as neural networks, partial least squares, and principal component regression to optimize the control of reactor systems. However, specific design methods and optimization of the neural network models in performing predictions have not been considered, and there has been room for improvement in the prediction technology related to prediction targets such as chemical reactions of synthetic resins.

SUMMARY

One or more embodiments of the present disclosure made in view of such circumstances improve the prediction technology related to the prediction targets.

(1) A method for prediction in one or more embodiments of the present disclosure is a method for prediction executed by an information processing device, the method comprising:

training a neural network model based on actual data on a prediction target; and predicting an objective factor related to the prediction target based on a plurality of explanatory factors related to the prediction target by the neural network model, in which the neural network model comprises an input layer, an intermediate layer, and an output layer, and a coefficient of an activation function of the intermediate layer is larger than a coefficient of an activation function of the output layer.

(2) A method for prediction in one or more embodiments of the present disclosure is the method for prediction according to (1), in which the activation function of the intermediate layer is a sigmoid function determined by below Mathematical Formula (1), and the activation function of the output layer is a sigmoid function determined by below Mathematical Formula (2), and $\alpha_1$ and $\alpha_2$ satisfy $\alpha_1 > \alpha_2$:

[Mathematical Formula 1]

$$f^1(u_j^1) = \frac{1}{1 + e^{-a_1 u_j^1}} \tag{1}$$

$$f^2(u_j^2) = \frac{1}{1 + e^{-a_2 u_j^2}} \tag{2}$$

where $$f^1(u_j^1)$$

is the activation function of the intermediate layer; $\alpha_1$ is the coefficient of the activation function of the intermediate layer;

$$u_j^1$$

is an input value input to a j-th element of the intermediate layer;

$$f^2(u_j^2)$$

is the activation function of the output layer; $\alpha_2$ is the coefficient of the activation function of the output layer; and $$u_j^2$$

is an input value input to a j-th element of the output layer.

(3) A method for prediction in one or more embodiments of the present disclosure is the method for prediction according to (1) or (2), in which the prediction target includes a polycondensation reaction and an addition polymerization reaction.

(4) A method for prediction in one or more embodiments of the present disclosure is the method for prediction according to any one of (1) to (3), in which the number of elements in the intermediate layer is 1.1 times or more and less than 6 times the number of the explanatory factors.

(5) A method for prediction in one or more embodiments of the present disclosure is the method for prediction according to any one of (1) to (4), in which a numerical value range of the explanatory factors input to the input layer is 0 or more and 1 or less, and a numerical value range of the objective factor output from the output layer is 0.2 or more and 0.8 or less.

(6) An information processing device in one or more embodiments of the present disclosure comprises a processor, in which the processor:

trains a neural network model based on actual data on a prediction target, and predicts an objective factor related to the prediction target based on explanatory factors related to the prediction target by the neural network model, and the neural network model comprises an input layer, an intermediate layer, and an output layer, and a coefficient of an activation function of the intermediate layer is larger than a coefficient of an activation function of the output layer.

(7) A non-transitory computer-readable recording medium in one or more embodiments of the present disclosure is a non-transitory computer-readable recording medium storing instructions executed by an information processing device that comprises a processor, the instructions causing the processor to execute:

training a neural network model based on actual data on a prediction target; and predicting an objective factor related to the prediction target based on explanatory factors related to the prediction target by the neural network model, in which the neural network model comprises an input layer, an intermediate layer, and an output layer, and a coefficient of an activation function of the intermediate layer is larger than a coefficient of an activation function of the output layer.

With the method for prediction, the information processing device, and the recording medium storing instructions in one or more embodiments of the present disclosure, the prediction technology related to the prediction target can be improved.

DETAILED DESCRIPTION OF EMBODIMENTS

Figure 1:
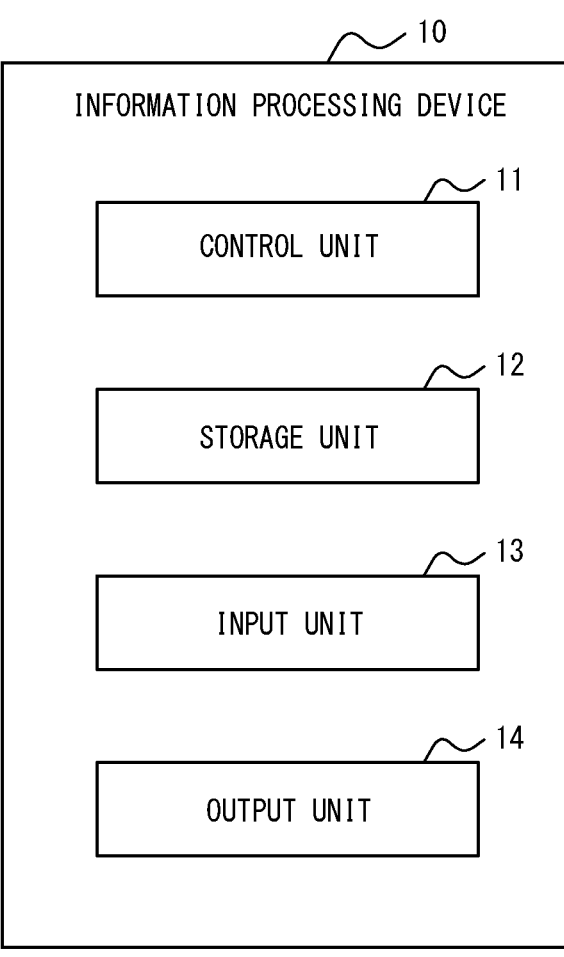
FIG. 1 is a block diagram illustrating the schematic configuration of an information processing device that performs prediction related to chemical reactions of synthetic resins in one or more embodiments.

Hereinafter, the method for performing the prediction related to the prediction target in embodiments of the present disclosure will be described with reference to the drawings. The prediction target according to one or more embodiments includes chemical reactions of synthetic resins. Hereinafter, in one or more embodiments, the case where the prediction target is a chemical reaction of a synthetic resin will be described as one example. Here, the chemical reaction of the synthetic resin includes a polycondensation reaction and an addition polymerization reaction. Examples of the main polymer materials synthesized by the polycondensation reactions include polyesters, polyamides, polyethylene terephthalate, urea resins, phenolic resins, silicone resins, alkyd resins, alkyd resin polyethers, polyglucosides, melamine resins, and polycarbonates. Examples of the main polymer materials synthesized by the addition polymerization reactions include poly(meth)acrylic acid esters, polyethylene, polypropylene, polystyrene, polyvinyl chloride, polyvinyl acetate, polyvinylidene chloride, polyacrylonitrile, and polytetrafluoroethylene.

In each of the drawings, identical or equivalent parts are assigned the same symbols. In the description of one or more embodiments, descriptions of the identical or equivalent parts are omitted or simplified as appropriate.

First, the overview of one or more embodiments will be described. In the method for performing the prediction related to the chemical reaction of the synthetic resin in one or more embodiments, a neural network model is trained based on actual data on the chemical reaction of the synthetic resin. The trained neural network model is used to predict an objective factor related to the chemical reaction of the synthetic resin based on a plurality of explanatory factors related to the chemical reaction of the synthetic resin. Here, the neural network model according to one or more embodiments includes an input layer, an intermediate layer, and an output layer, and the coefficient of an activation function of the intermediate layer is larger than the coefficient of an activation function of the output layer.

Therefore, one or more embodiments are characterized in that the neural network model includes the input layer, the intermediate layer, and the output layer, and the coefficient of the activation function of the intermediate layer is larger than the coefficient of the activation function of the output layer. In the case where the prediction related to the chemical reaction of the synthetic resin is performed, the learning process can be optimized and the prediction accuracy can be improved by setting the coefficient of the activation function of the intermediate layer larger than the coefficient of the activation function of the output layer, as described later. Therefore, according to one or more embodiments, the prediction technology related to the chemical reaction of the synthetic resin can be improved.

(Configuration of Information Processing Device)

Subsequently, referring to FIG. 1, each configuration of an information processing device 10 will be described in detail. The information processing device 10 is an arbitrary device used by users. For example, personal computers, server computers, general-purpose electronic devices, or dedicated electronic devices can be employed as the information processing device 10.

As illustrated in FIG. 1, the information processing device 10 includes a control unit (or a processor) 11, a storage unit (or a storage) 12, an input unit (or an input interface) 13, and an output unit (or an output interface) 14.

The control unit 11 includes at least one processor, at least one dedicated circuit, or a combination thereof. The processor is a general-purpose processor such as a central processing unit (CPU) or a graphics processing unit (GPU), or a dedicated processor specialized for specific processing. The dedicated circuit is, for example, a field-programmable gate array (FPGA) or an application specific integrated circuit (ASIC). The control unit 11 executes processes associated with the operation of the information processing device 10 while controlling each part of the information processing device 10.

The storage unit 12 includes at least one semiconductor memory, at least one magnetic memory, at least one optical memory, or a combination of at least two of these memories. The semiconductor memory is, for example, a random-access memory (RAM) or a read-only memory (ROM). The RAM is, for example, a static random-access memory (SRAM) or a dynamic random-access memory (DRAM). The ROM is, for example, an electrically erasable programmable read-only memory (EEPROM). The storage unit 12 functions, for example, as a main memory device, an auxiliary memory device, or a cache memory. In the storage unit 12, data used in the operation of the information processing device 10 and data obtained by the operation of the information processing device 10 are stored.

The input unit 13 includes at least one interface for input. The interface for input is, for example, physical keys, capacitive keys, pointing devices, or touch screens integrated with displays. The interface for input may be, for example, a microphone that accepts voice input or a camera that accepts gesture input. The input unit 13 accepts operations to input data used in the operation of the information processing device 10. The input unit 13 may be connected to the information processing device 10 as an external input device instead of being provided in the information processing device 10. For example, any method such as universal serial bus (USB), high-definition multimedia interface (HDMI) (registered trademark), or Bluetooth (registered trademark) can be used as the connection method.

The output unit 14 includes at least one interface for output. The interface for output is, for example, a display that outputs information in the form of images. The display is, for example, a liquid crystal display (LCD) or an electroluminescence (EL) display. The output unit 14 displays and outputs data obtained by the operation of the information processing device 10. The output unit 14 may be connected to the information processing device 10 as an external output device instead of being provided in the information processing device 10. For example, any method such as USB, HDMI (registered trademark), or Bluetooth (registered trademark) can be used as the connection method.

The functions of the information processing device 10 are achieved by executing program or instructions according to one or more embodiments on a processor corresponding to the information processing device 10. In other words, the functions of the information processing device 10 are achieved by the software. The instructions cause the computer to function as the information processing device 10 by causing the computer to execute the operations of the information processing device 10. In other words, the computer functions as the information processing device 10 by executing the operation of the information processing device 10 in accordance with the instructions.

In one or more embodiments, the instructions can be recorded on a computer-readable recording medium. The computer-readable recording media include non-transient (non-transitory) computer-readable media, for example, magnetic recording devices, optical discs, magneto-optical recording media, or semiconductor memories.

A part of or all of the functions of the information processing device 10 may be achieved by a dedicated circuit corresponding to the control unit 11. In other words, a part of or all of the functions of the information processing device 10 may be achieved by hardware.

In one or more embodiments, the storage unit 12 stores, for example, actual data and prediction models. The actual data and the prediction model may be stored in an external device separate from the information processing device 10. In this case, the information processing device 10 may be equipped with an interface for external communication. The interface for communication may be either interface of a wired communication or interface of wireless communication. In the case of the wired communication, the interface for communication is, for example, a LAN interface or USB. In the case of the interface for wireless communication, the interface for communication is, for example, an interface compliant with mobile communication standards such as LTE, 4G, or 5G, or an interface compliant with short-range wireless communication such as Bluetooth (registered trademark). The interface for communication can receive data used in the operation of the information processing device 10 and can transmit data obtained by the operation of the information processing device 10.

(Operation of Information Processing Device)

Figure 2:
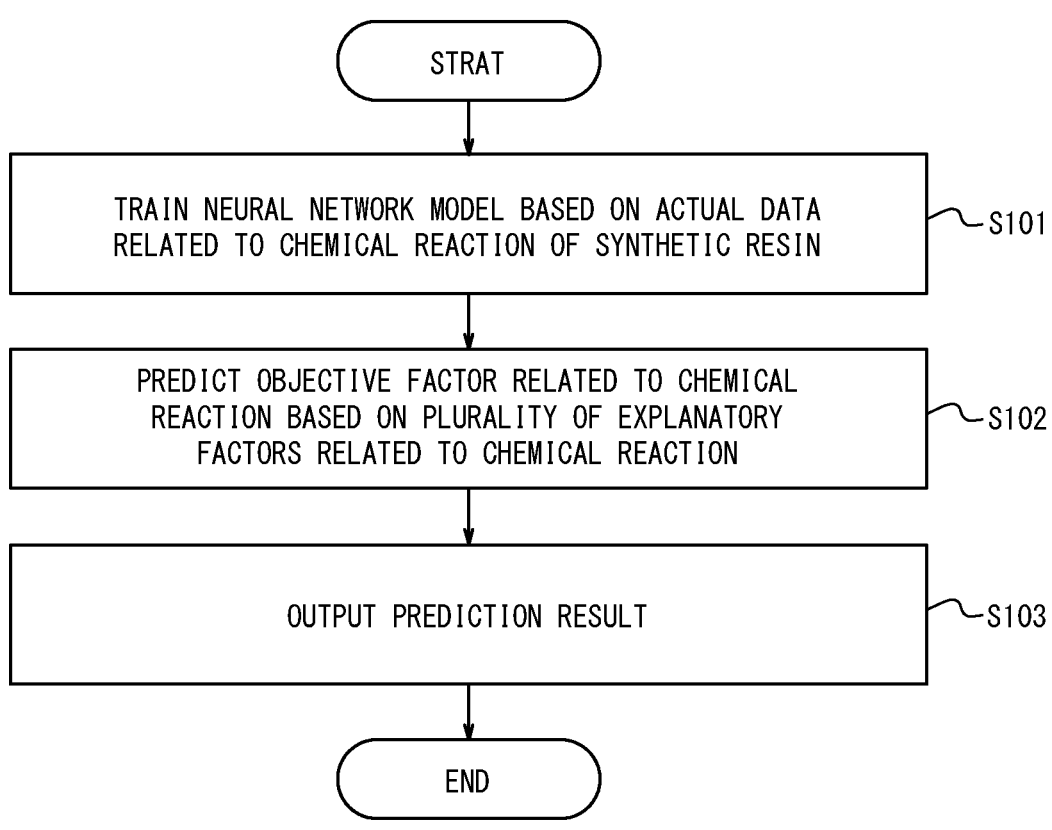
FIG. 2 is a flowchart illustrating operations of the information processing device that performs prediction related to the chemical reactions of the synthetic resins in one or more embodiments.

Subsequently, with reference to FIG. 2, the operation of the information processing device 10 according to one or more embodiments will be described.

Step S101: The control unit 11 of the information processing device 10 trains a neural network model based on actual data on the chemical reaction of the synthetic resin. The actual data includes the explanatory factors and the objective factor related to the chemical reaction of the synthetic resin. Such explanatory factors and objective factor are appropriately selected depending on the target chemical reaction of the synthetic resin to be predicted. The target chemical reaction of the synthetic resin to be predicted includes a polycondensation reaction and an addition polymerization reaction, for example. The polycondensation reaction includes a dehydration-condensation reaction. For example, in the case where the prediction related to the dehydration-condensation reaction is performed, the experimental data include the explanatory factors and the objective factor related to the dehydration-condensation reaction. For example, the explanatory factors may include feature values and the like related to the dehydration and temperature rising processes. The objective factor may also include a hydroxyl value, an acid value, and the like. In other words, the control unit 11 trains the neural network model using these explanatory factors and objective factor included in the actual data as the training data.

Any method can be employed to acquire the actual data. For example, the control unit 11 acquires the actual data from the storage unit 12. The control unit 11 may also acquire the actual data by accepting input of the actual data from the user by the input unit 13. Alternatively, the control unit 11 may acquire such actual data from an external device that stores the actual data through an interface for communication.

The neural network model trained based on the training data is cross-validated based on known data. As a result of such cross-validation, in the case where an accuracy is within a practical range, the prediction related to the chemical reaction of the synthetic resin is performed using the neural network model.

Step S102: The control unit 11 predicts the objective factor related to the chemical reaction of the synthetic resin based on the explanatory factors related to the chemical reaction of the synthetic resin. For example, the control unit 11 may acquire the objective factor by accepting input of the explanatory factors from the user by the input unit 13.

Step S103: The control unit 11 outputs the prediction result obtained in Step S102 using the output unit 14.

Here, one or more embodiments are characterized in that the coefficients of the activation function are different between the intermediate layer and the output layer. Specifically, in one or more embodiments, the coefficient of the activation function of the intermediate layer is characterized by being larger than the coefficient of the activation function of the output layer.

Figure 3:
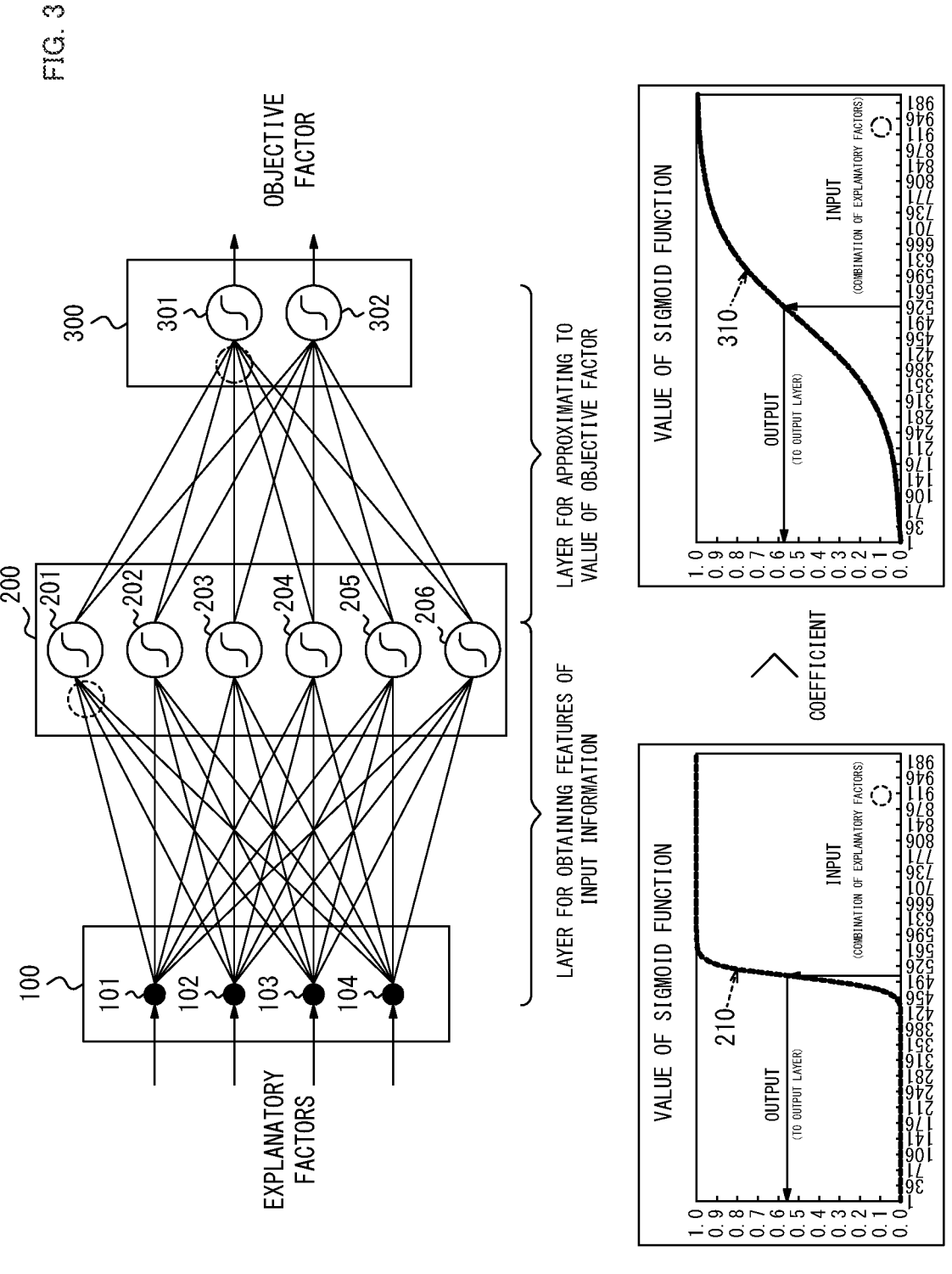
FIG. 3 is a conceptual diagram of a neural network model in one or more embodiments.

FIG. 3 is a conceptual diagram of the neural network model according to one or more embodiments. The neural network model according to one or more embodiments includes an input layer 100, an intermediate layer 200, and an output layer 300. The neural network model in one or more embodiments is fully connected. In one or more embodiments, the number of layers in the neural network model is, for example, 2. Such number of layers is the number of layers excluding the input layer. By setting the number of layers in the neural network model to 2, a model configuration can be prevented from becoming inappropriate to the physical phenomena in the chemical reaction of the synthetic resin. In other words, the number of layers of neural network model can be kept to minimum necessary, whereby the model configuration suitable for the physical phenomena in the chemical reaction of the synthetic resin can be achieved. The number of layers of the neural network model according to one or more embodiments is not limited to this number of layers, and may be three layers or more. In the case where the number of layers in the neural network model is three or more, as the layer of the neural network model becomes more front side, the coefficient of the activation function may be set larger.

The input layer 100 includes a plurality of elements 101 to 104 (also referred to as input elements 101 to 104). In the neural network model illustrated in FIG. 3, the number of the input elements is 4. The input elements 101 to 104 are also referred to as the first to fourth elements, respectively. In the input elements 101 to 104, each of the explanatory factors is input. The number of the input elements, however, is not limited to this number.

The intermediate layer 200 includes a plurality of elements 201 to 206 (also referred to as intermediate elements 201 to 206). In the neural network model illustrated in FIG. 3, the number of the intermediate elements is 6. The intermediate elements 201 to 206 are also referred to as the first to sixth elements, respectively. The number of intermediate elements, however, is not limited to this number.

The output layer 300 includes a plurality of elements 301 and 302 (also referred to as output elements 301 and 302). In the neural network model illustrated in FIG. 3, the number of the output elements is 2. The output elements 301 and 302 are also referred to as the first and second elements, respectively. The number of the output elements, however, is not limited to this number.

The values input from the input elements 101 to 104 of the input layer 100 to the intermediate elements 201 to 206 of the intermediate layer 200 are converted in the intermediate layer 200 based on the activation function of the intermediate layer 200. The converted values are output to the elements 301 and 302 of the output layer 300. The activation function of the intermediate layer 200 is, for example, a sigmoid function. A graph 210 illustrates one example of the activation function of the intermediate layer 200. The values input from the intermediate elements 201 to 206 of the intermediate layer 200 to the output elements 301 and 302 of the output layer 300 are converted in the output layer 300 based on the activation function of output layer 300 and output. The activation function of the output layer 300 is, for example, the sigmoid function. A graph 310 illustrates one example of the activation function of the output layer 300. Specifically, the activation functions related to the intermediate layer and the output layer are, for example, the respective sigmoid functions determined by the following formulas (1) and (2).

[Mathematical Formula 2]

$$f^1(u_j^1) = \frac{1}{1 + e^{-a_1 u_j^1}} \tag{1}$$

$$f^2(u_j^2) = \frac{1}{1 + e^{-a_2 u_j^2}} \tag{2}$$

Here, $$f^1(u_j^1)$$

is the activation function of the intermediate layer 200, $\alpha_1$ is the coefficient of the activation function of the intermediate layer 200, and $$u_j^1$$

is the input value input to the j-th element of the intermediate layer 200. In the example in FIG. 3, the number of the intermediate elements is 6, and this j takes the value from 1 to 6.

$$f^2(u_j^2)$$

is the activation function relative to the output layer 300, $\alpha_2$ is the coefficient of the activation function of the output layer 300, and $$u_j^2$$

is the input value input to the j-th element of the output layer 300. In the example in FIG. 3, j is 1 or 2 because the number of the output elements is 2. As described above, in the neural network model according to one or more embodiments, the coefficient of the activation function of the intermediate layer 200 is larger than the coefficient of the activation function of the output layer 300. In other words, $\alpha_1$ and $\alpha_2$ in the neural network model according to one or more embodiments are characterized by satisfying $\alpha_1 > \alpha_2$.

In the neural network model according to one or more embodiments, the coefficient of the activation function of the intermediate layer is larger than the coefficient of the activation function of the output layer. This allows the configuration of the neural network model to be optimized at the time of performing the prediction related to the chemical reaction of the synthetic resin. Specifically, in the neural network model for performing the prediction related to the chemical reaction of the synthetic resin, change in the explanatory factors is desirably viewed as obvious change. Therefore, by setting the coefficient of the activation functions related to the intermediate layer larger than the coefficient of the activation functions related to the output layer, the change in the input values to the intermediate layer can be transmitted to the output layer as the obvious change. On the other hand, in the output layer of the neural network model for performing the prediction related to the chemical reaction of the synthetic resin, the values of the training data and the objective factor are required to be converged. Therefore, the coefficient of the activation function of the output layer is set smaller than the coefficient of the activation function of the intermediate layer. By doing so, the value of the objective factor output from the output layer is finely adjusted.

By setting the coefficients of the activation functions between the intermediate layer and the output layer to be different, the learning process of the neural network model is optimized. Specifically, the updated amount of the weight variables in the output layer and the intermediate layer during the learning process can be adjusted by changing the coefficient of the activation function. In addition, updating the weight variables provides a significant impact on the learning process. Therefore, the learning process may be optimized based on the adjustment of the updated amount. Hereinafter, the updated amount of the weight variables in an L-layer neural network model will be described.

First, the updated amount of the weight variables in the L-th layer (output layer) will be described. The updated amount of such weight variables is determined by Mathematical Formula (3) described below based on the partial derivative of the loss function.

[Mathematical Formula 3]

$$\text{(Updated amount of weight variables in } L-th \text{ layer)} = -1 \times \varepsilon \times \frac{\partial E}{\partial w_{ij}^L} \tag{3}$$

Here, $\varepsilon$ is a learning constant, E is the loss function, and $$w_{ij}^L$$

the weight variable between the i-th intermediate element of the L−1-th layer and the j-th element of the L-th layer of the neural network model.

The partial derivative of the loss function on the right-hand side of Mathematical Formula (3) can be transformed based on the chain rule of differentiation as follows.

[Mathematical Formula 4]

$$\frac{\partial E}{\partial w_{ij}^L} = \frac{\partial E}{\partial u_j^L} \frac{\partial u_j^L}{\partial w_{ij}^L} \tag{4}$$

Here, $$u_j^L$$

is the input value to the j-th element in the L-th layer of the neural network model. The neural network model in one or more embodiments is fully connected. Therefore, $$u_j^L$$

is a weighted linear sum of values obtained by multiplying the output values of the intermediate elements in the L−1 layer of the neural network model by the respective weight variables $$w_{ij}^L.$$

When the first term on the right-hand side of Mathematical Formula (4) is defined as $$\delta_j^L,$$

Mathematical Formula (4) can be transformed as follows.

[Mathematical Formula 5]

$$\frac{\partial E}{\partial u_j^L} \frac{\partial u_j^L}{\partial w_{ij}^L} = \delta_j^L z_i^{L-1} \tag{5}$$

Here, $$z_i^{L-1}$$

is the output value of the i-th intermediate element of the L−1-th layer of the neural network. The formula transformation of Mathematical Formula (5) is based on the relational formula of Mathematical Formula (6) below.

[Mathematical Formula 6]

$$\frac{\partial u_j^L}{\partial w_{ij}^L} = z_i^{L-1} \tag{6}$$

The first term $$\delta_j^L$$

of Mathematical Formula (5) can be transformed based on the chain rule of differentiation as follows.

[Mathematical Formula 7]

$$\delta_j^L = \frac{\partial E}{\partial z_j^L} \frac{\partial z_j^L}{\partial u_j^L} \tag{7}$$

Mathematical Formula (7) can be transformed as follows.

[Mathematical Formula 8]

$$\frac{\partial E}{\partial z_j^L} \frac{\partial z_j^L}{\partial u_j^L} = \frac{\partial E}{\partial y_j} \frac{\partial z_j^L}{\partial u_j^L} \tag{8}$$

Here, $y_j$ is the output value of the j-th element of the L-th layer (that is, the output layer) of the neural network, which is the same value as $$z_j^L.$$

In the case where the loss function is a squared error function, the loss function is represented as follows.

[Mathematical Formula 9]

$$E = \frac{1}{2} \sum_i (y_i - d_i)^2 \qquad (9)$$

Here, $d_i$ is the i-th value of the training data.

When the loss function is the squared error function, Mathematical Formula (8) can be transformed as follows.

[Mathematical Formula 10]

$$\frac{\partial E}{\partial y_j} \frac{\partial z_j^L}{\partial u_j^L} = (y_j - t_j) \frac{\partial z_j^L}{\partial u_j^L}. \qquad (10)$$

When the activation function of the L-th layer is the sigmoid function, the activation function is represented as follows.

[Mathematical Formula 11]

$$f^L(u_j^L) = \frac{1}{1 + e^{-a^L u_j^L}} \qquad (11)$$

Here, $f^L$ is the activation function of the L-th layer and $a^L$ is the coefficient of the sigmoid function of the L-th layer (output layer).

The second term on the right-hand side of Mathematical Formula (10) can be transformed based on Mathematical Formula (11) as follows.

[Mathematical Formula 12]

$$\frac{\partial z_j^L}{\partial u_j^L} = \frac{\partial f^L(u_j^L)}{\partial u_j^L} = a^L f^L(u_j^L) \; (1 - f^L(u_j^L)) \qquad (12)$$

Mathematical Formula (12) can be further transformed as follows.

[Mathematical Formula 13]

$$a^L f^L(u_j^L)(1 - f^L(u_j^L)) = a^L z_j^L(1 - z_j^L) = a^L y_j(1 - y_j) \qquad (13)$$

Based on Mathematical Formula (5) to Mathematical Formula (13), Mathematical Formula (4) can be transformed as follows.

[Mathematical Formula 14]

$$\frac{\partial E}{\partial w_{ij}^L} = (y_j - t_j)\frac{\partial z_j^L}{\partial u_j^L}z_j^{L-1} = a^L(y_j - t_j)(1 - y_j)y_j z_i^{L-1} \qquad (14)$$

All of the variables on the right-hand side of Mathematical Formula (14) are values obtained by numerical calculation. Therefore, the value on the left-hand side can be determined by the numerical calculation. Therefore, the updated amount of each weight variable in the output layer represented by Mathematical Formula (3) can be obtained based on numerical calculations.

Subsequently, the updated amount of the intermediate layer in the learning process of the neural network model will be described. The updated amount of the weight variables of the intermediate layer is determined by the following Mathematical Formula (15) based on the partial derivative of the loss function.

[Mathematical Formula 15]

$$\text{(Updated amount of weight variables in } l-th \text{ layer)} = \qquad (15)$$
$$-1 \times \varepsilon \times \frac{\partial E}{\partial w_{ij}^l}$$

Here, $l$ represents the l-th layer of the neural network. In other words, the l-th layer corresponds to the intermediate layer. is the weight variable between the i-th intermediate element of the l−1-th layer and the j-th element of the l-th layer of the neural network.

The partial derivative of the loss function on the right-hand side of Mathematical Formula (15) can be transformed based on the chain rule of differentiation as follows.

[Mathematical Formula 16]

$$\frac{\partial E}{\partial w_{ij}^l} = \frac{\partial E}{\partial u_j^l} \frac{\partial u_j^l}{\partial w_{ij}^l} \qquad (16)$$

Here, $$u_j^l$$

is the input value to the j-th element of the l-th layer of the neural network. The neural network model in one or more embodiments is fully connected. Therefore, $$u_j^l$$

is a weighted linear sum of values obtained by multiplying the output values of the intermediate elements in the l−1-th layer of the neural network by the respective weight variables $$w_{ij}^l.$$

When the first term on the right-hand side of Mathematical Formula (16) is defined as $$\delta_j^l,$$

Mathematical Formula (16) can be transformed as follows.

[Mathematical Formula 17]

$$\frac{\partial E}{\partial u_j^l}\frac{\partial u_j^l}{\partial w_{ij}^l} = \delta_j^l z_i^{l-1} \tag{17}$$

Here, $$z_i^{l-1}$$

is the output value of the i-th intermediate element of the l−1-th layer of the neural network. The formula transformation of Mathematical Formula (17) is based on the relational formula of Mathematical Formula (18) below.

[Mathematical Formula 18]

$$\frac{\partial u_j^l}{\partial w_{ij}^l} = z_i^{l-1} \tag{18}$$

The first term of $$\delta_j^l$$

in Mathematical Formula (17) can be transformed based on the chain rule of differentiation as follows.

[Mathematical Formula 19]

$$\delta_j^l = \Sigma_k \frac{\partial E}{\partial u_k^{l+1}}\frac{\partial u_k^{l+1}}{\partial u_j^l} = \Sigma_k \delta_j^{l+1}\frac{\partial u_k^{l+1}}{\partial z_j^l}\frac{\partial z_j^l}{\partial u_j^l} \tag{19}$$

The right-hand side of Mathematical Formula (19) can be further transformed as follows.

[Mathematical Formula 20]

$$\Sigma_k \delta_k^{l+1}\frac{\partial u_k^{l+1}}{\partial z_j^l}\frac{\partial z_j^l}{\partial u_j^l} = \Sigma_k \delta_k^{l+1}w_{jk}^l\{f^l(u_j^l)\}' \tag{20}$$

When the activation function of the l-th layer is the sigmoid function, the activation function is represented as follows.

[Mathematical Formula 21]

$$f^l(u_j^l) = \frac{1}{1 + e^{-a^l u_j^l}} \tag{21}$$

Here, $f^l$ is the activation function of the l-th layer and $a^l$ is the coefficient of the sigmoid function of the l-th layer.

When the activation function of the l-th layer is the sigmoid function described above, the right-hand side of Mathematical Formula (20) can be transformed as follows.

[Mathematical Formula 22]

$$\Sigma_k \delta_k^{l+1}w_{jk}^{l+1}\{f^l(u_j^l)\}' = a^l f^l(u_j^l)(1 - f^l(u_j^l))\sum_k \delta_k^{l+1}w_{jk}^{l+1} \tag{22}$$

Mathematical Formula (22) can be further transformed as follows.

[Mathematical Formula 23]

$$a^l f^l(u_j^l)(1 - f^l(u_j^l))\sum_k \delta_k^{l+1}w_{jk}^{l+1} = a^l z_j^l(1 - z_j^l)\sum_k \delta_k^{l+1}w_{jk}^{l+1} \tag{23}$$

Based on Mathematical Formula (17) to Mathematical Formula (23), Mathematical Formula (16) can be transformed as follows.

[Mathematical Formula 24]

$$\frac{\partial E}{\partial w_{ij}^l} = \delta_j^l z_i^{l-1} = a^l z_j^l(1 - z_j^l)z_i^{l-1}\sum_k \delta_k^{l+1}w_{jk}^{l+1} \tag{24}$$

All of the variables on the right-hand side of Mathematical Formula (24) are values obtained by numerical calculation. Specifically, $$\delta_k^{l+1}$$

is a value sequentially determined from $$\delta_j^l$$

of the output layer. Other variables are values determined by numerical calculations. Therefore, the updated amount of each weight variable of the intermediate layer represented in Equation (15) can be obtained based on numerical calculations.

As represented in Mathematical Formula (14) and Mathematical Formula (24), the coefficients of the activation function are relevant in the process of calculating the updated amount of each weight variable. Specifically, when the activation functions of the intermediate layer and the output layer are the sigmoid functions, the respective updated amounts are proportional to $a^l$ and $a^L$ of the activation function. In other words, by changing the coefficients $a^l$ and $a^L$ of the sigmoid function, the updated amount of the weight variables can be adjusted and the learning process of the neural network model can be optimized.

Specifically, in the neural network model at the time of performing prediction related to the chemical reaction of synthetic resin, the updated amount of the weight variable related to the intermediate layer may be set to relatively large. This allows the weight variables in the intermediate layer to vary more significantly during the learning process, and thus changes in the input values to the intermediate layer to be transferred to the output layer as obvious changes. On the other hand, the updated amount of weight variables related to the output layer may be set to relatively small. This allows the weight variables in the output layer to vary less during the learning process and thus the values of the training data and the objective factor to be easily converged.

In addition, by satisfying $a^l > a^L$, an arbitrary smooth function can be approximated with sufficient accuracy, eliminating the need to inadvertently increase the number of intermediate layers. This allows sufficient accuracy to be obtained even when the intermediate layer is one layer. Preparing fewer intermediate layers directly leads to reduction in generation of over-fitting and thus provides a secondary effect on stability of the learning process and, in addition, robustness of the model.

Figure 4:
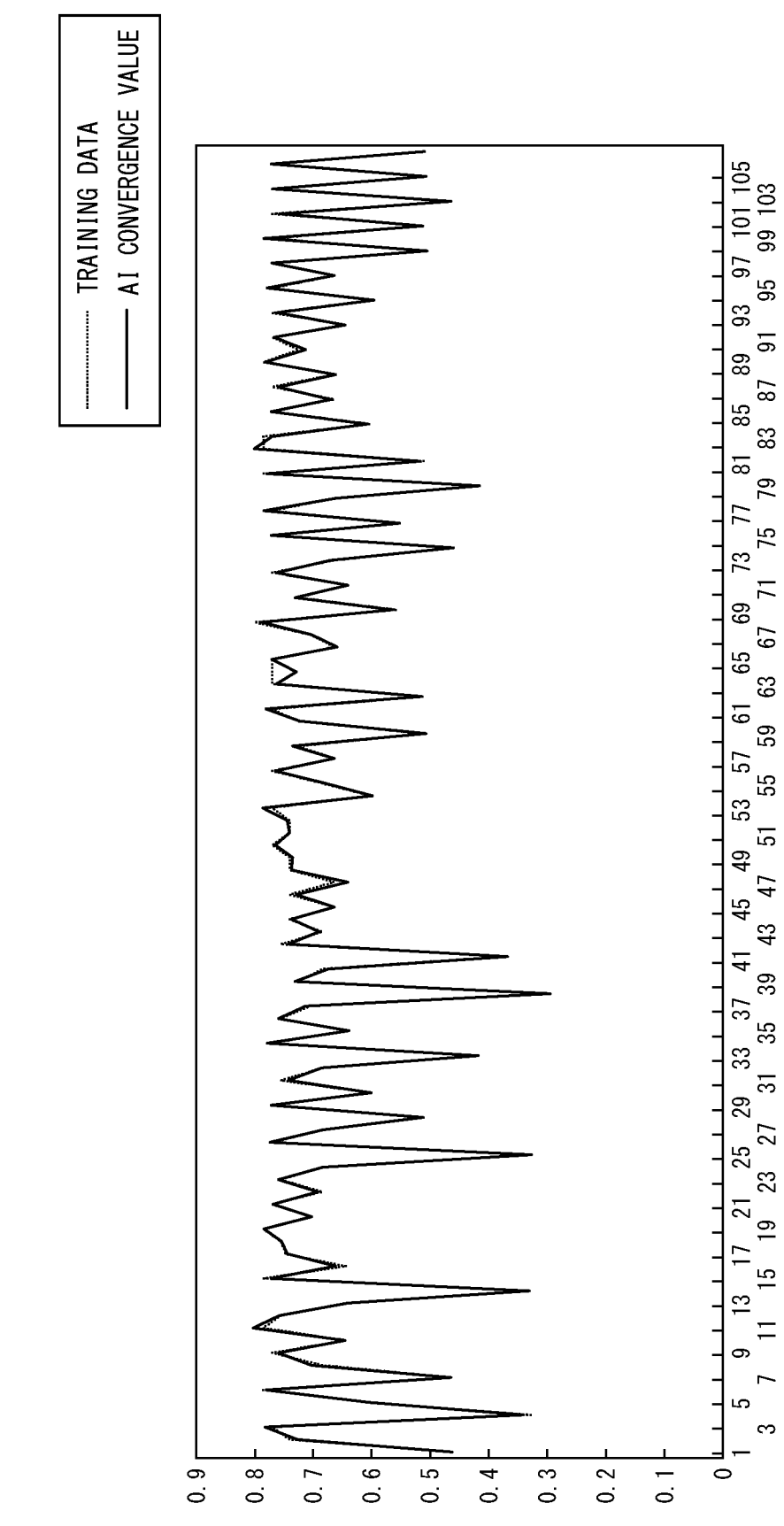
FIG. 4 is a graph illustrating learning convergence results of the neural network model in one or more embodiments.

In the neural network model according to one or more embodiments, the coefficient of the sigmoid function in the intermediate layer is, for example, 0.75 and the coefficient of the sigmoid function in the output layer is, for example, 0.1. FIG. 4 illustrates the learning convergence result of the neural network model of the prediction related to the chemical reaction of the synthetic resin when the coefficient of the sigmoid function in the intermediate layer is set to 0.75 and the coefficient of the sigmoid function in the output layer is set to 0.1. The training termination error is 0.003, the number of training cycles is 200,000, the number of the input factors is 13, the number of the intermediate elements is 20, and the number of the output factors is 1. As illustrated in FIG. 4, the values of the training data and the AI convergence values are almost identical and converge almost to limit values. As described above, in the neural network model for performing prediction related to the chemical reaction of the synthetic resin, a highly accurate prediction model can be obtained by setting the coefficient of the sigmoid function in the intermediate layer larger than the coefficient of the sigmoid function in the output layer.

Figure 5:
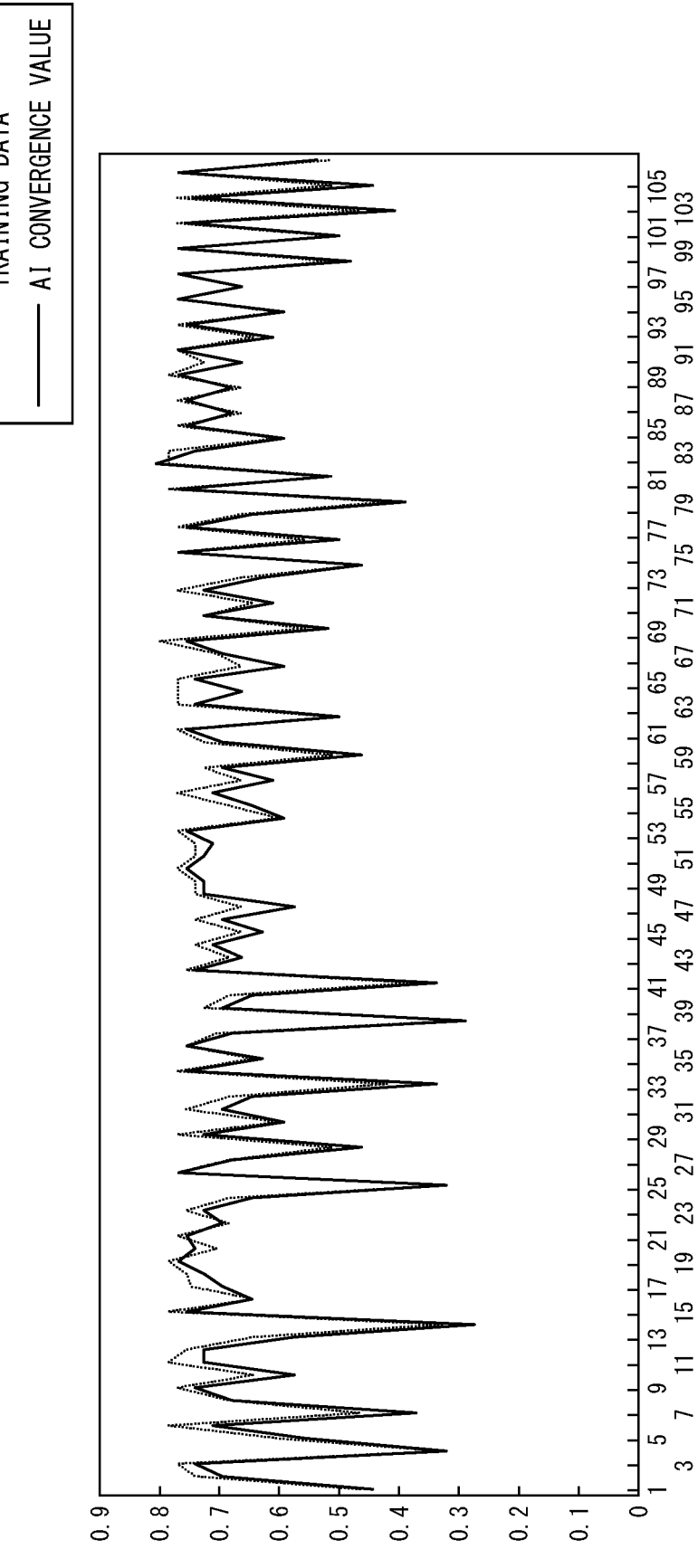
FIG. 5 is a graph illustrating learning convergence results of the neural network model related to Comparative Example.

As Comparative Example, FIG. 5 illustrates the learning convergence result of the neural network model in the case where the coefficient of the sigmoid function in the intermediate layer is set to 0.75 and the coefficient of the sigmoid function in the output layer is set to 0.75. The training error, the number of the training cycles, the number of the input factors, the number of the intermediate elements, and the number of the output factors are the same as the training conditions in FIG. 4. As illustrated in FIG. 5, the values of the training data and the AI convergence values differ in some parts and are less accurate than those in the neural network model illustrated in FIG. 4.

Figure 6:
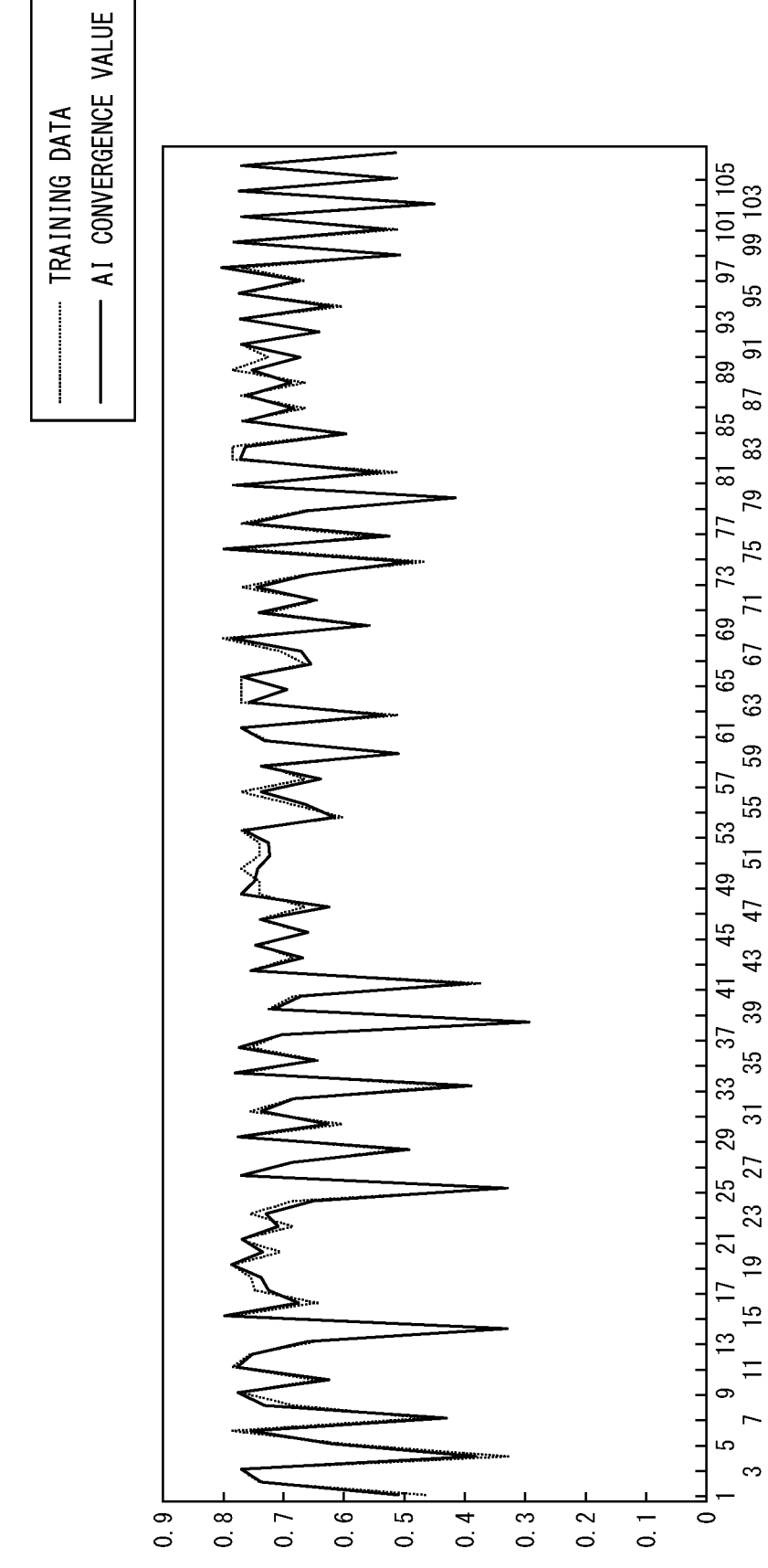
FIG. 6 is a graph illustrating learning convergence results of the neural network model related to Comparative Example.

As Comparative Example, FIG. 6 illustrates the learning convergence result of the neural network model when the coefficient of the sigmoid function in the intermediate layer is set to 0.1 and the coefficient of the sigmoid function in the output layer is set to 0.1. The training error, the number of the training cycles, the number of the input factors, the number of the intermediate elements, and the number of the output factors are the same as the training conditions in FIG. 4. As illustrated in FIG. 6, the values of the training data and the AI convergence values differ in some parts and are less accurate than those in the neural network model illustrated in FIG. 4.

Figure 7:
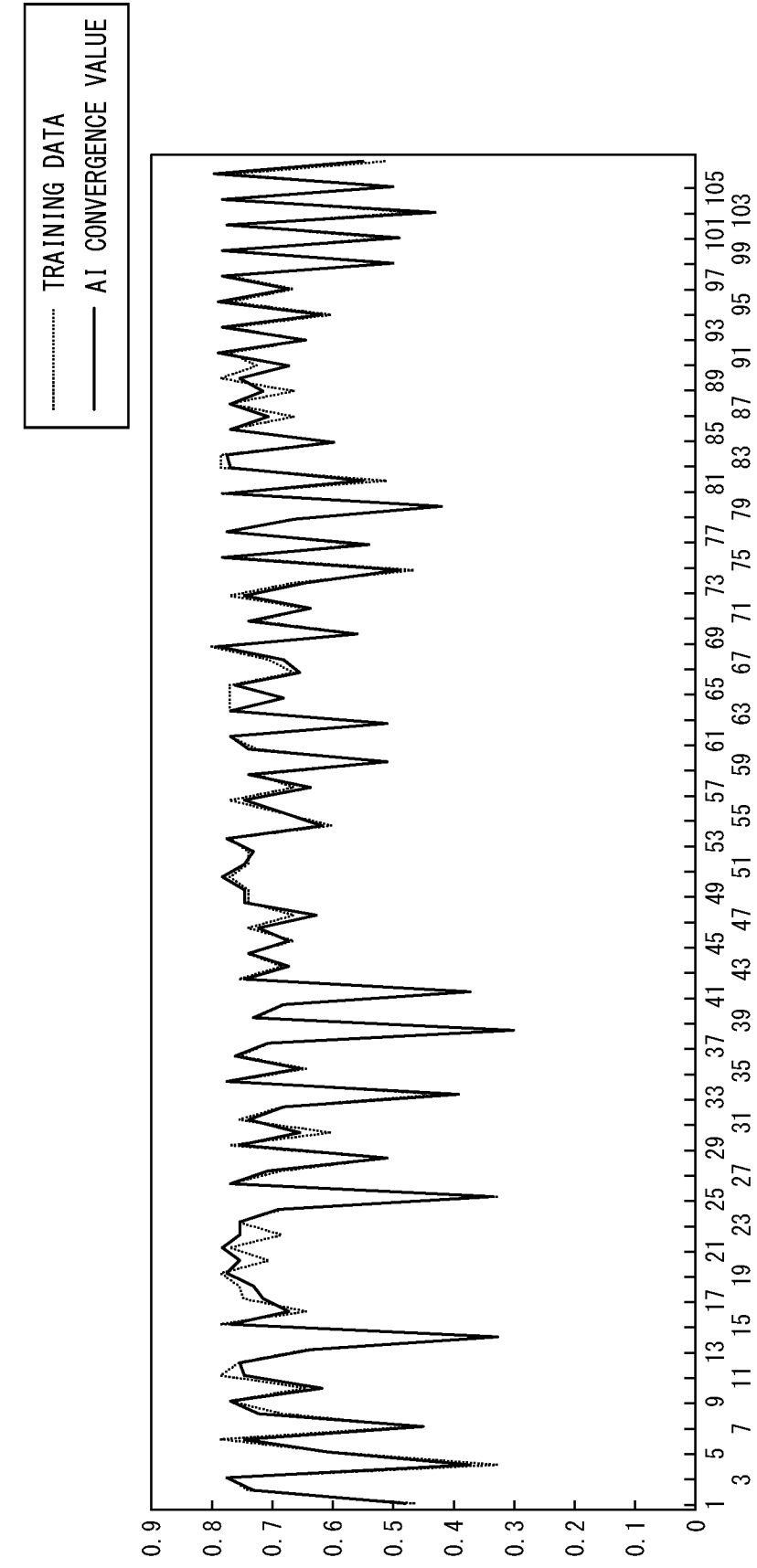
FIG. 7 is a graph illustrating learning convergence results of the neural network model related to Comparative Example.

As Comparative Example, FIG. 7 illustrates the learning convergence result of the neural network model in the case where the coefficient of the sigmoid function in the intermediate layer is set to 0.4 and the coefficient of the sigmoid function in the output layer is set to 0.4. The training error, the number of the training cycles, the number of the input factors, the number of the intermediate elements, and the number of the output factors are the same as the training conditions in FIG. 4. As illustrated in FIG. 7, the values of the training data and the AI convergence values differ in some parts and are less accurate than those in the neural network model illustrated in FIG. 4.

As can be seen from the above learning convergence results of the models in FIGS. 4 to 7, the neural network model for predicting the chemical reaction of the synthetic resin has the highest accuracy when the coefficient of the sigmoid function in the intermediate layer is larger than the coefficient of the sigmoid function in the output layer. As described above, according to one or more embodiments, the prediction technology for the chemical reaction of the synthetic resin can be improved.

In one or more embodiments, the hyperparameters of the neural network model may be appropriately adjusted. For example, the learning constant may be any value as long as the learning constant is the smallest value at which the correction operation of the weights can be performed by differential operations. For example, in one or more embodiments, the number of the intermediate elements of the neural network model may be 1.1 times or more and less than 6 times of the number of the explanatory factors (the number of the elements in the input layer). The number of the intermediate elements may be determined based on the number of the elements in the output layer. Specifically, for example, the number of the intermediate elements, the coefficient of the sigmoid function, and the number of training cycles can be adjusted as follows.

1. Number of Intermediate Elements
   The case where the number of output elements is 1:1.1 times to 3 times
   The case where the number of output elements is 2:1.1 times to 4.5 times
   The case where the number of output elements is 3:1.1 times to 6 times
2. Coefficients of Sigmoid Function
   Intermediate layer: 0.70 to 0.80
   Output layer: 0.095 to 0.15
3. Number of Training Cycles
   100,000 times to 200,000 times (the case where the training data is about 50 sets to about 100 sets)

In one or more embodiments, the numerical range of each explanatory factor and the numerical range of each objective factor may be appropriately adjusted. For example, the numerical range of the explanatory factor input to the input layer may be 0 or more and 1 or less and the numerical range of the objective factor output from the output layer may be 0.2 or more and 0.8 or less. As described above, the explanatory factor side may be set to the full scale of 0 or more and 1 or less, which the neural network can handle. On the other hand, by limiting the objective factor side to 0.2 or more and 0.8 or less, the search range as numerical values can be narrowed to facilitate the search in numerical calculations.

The case where the activation functions of the intermediate layer and the output layer are sigmoid functions is described in one or more embodiments. However, the activation functions are not limited to the sigmoid functions. For example, the activation functions of the intermediate layer and the output layer may be functions such as a hyperbolic tangent function (tan h function) and a ramp functions (ReLU).

In one or more embodiments, the case where the prediction target is the chemical reaction of the synthetic resin is described as one example. The prediction target, however, is not limited to this case. The prediction target may be, for example, the prediction of a physical or chemical phenomenon such as a chemical reaction of any substance. The prediction target may not necessarily be a physical or chemical phenomenon and the like. In other words, the technology according to one or more embodiments can be used for the whole modeling using neural networks and the like.

Although the present disclosure has been described based on the drawings and examples, it should be noted that those skilled in the art can easily make changes and modifications based on the present disclosure. Therefore, it should be noted that these changes and modifications are included within the scope of the present disclosure. For example, the functions and the like included in the units, steps, or the like can be rearranged so as not to be logically inconsistent, and pluralities of units, steps, or the like can be combined to one or divided.

REFERENCE SIGNS LIST

10 information processing device
11 control unit
12 storage unit
13 input unit
14 output unit
100 input layer
200 intermediate layer
300 output layer
101 to 104, 301 to 206, and 301 and 302 element
210 and 310 graph

The invention claimed is:

1. A method for prediction executed by an information processing device, the method comprising:

training a neural network model based on actual data on a prediction target; and predicting an objective factor related to the prediction target based on explanatory factors related to the prediction target by the neural network model, wherein the neural network model comprises an input layer, an intermediate layer, and an output layer, and a coefficient of an activation function of the intermediate layer is larger than a coefficient of an activation function of the output layer.

2. The method for prediction according to claim 1, wherein the activation function of the intermediate layer is a sigmoid function determined by below Mathematical Formula (1), and the activation function of the output layer is a sigmoid function determined by below Mathematical Formula (2), and $\alpha1$ and $\alpha2$ satisfy $\alpha1 > \alpha2$:

$$f^{1}\left(u_{j}^{1}\right) = \frac{1}{1 + e^{-a_{1}u_{j}^{1}}} \tag{1}$$

$$f^{2}\left(u_{j}^{2}\right) = \frac{1}{1 + e^{-a_{2}u_{j}^{2}}} \tag{2}$$

where $$f^{1}\left(u_{j}^{1}\right)$$

is the activation function of the intermediate layer;
  $\alpha1$ is the coefficient of the activation function of the intermediate layer;

$$u_{j}^{1}$$

is an input value to a j-th element of the intermediate layer;

$$f^{2}\left(u_{j}^{2}\right)$$

is the activation function of the output layer,
  $\alpha2$ is the coefficient of the activation function of the output layer; and $$u_{j}^{2}$$

is an input value to a j-th element of the output layer.

3. The method for prediction according to claim 2, wherein the prediction target includes a polycondensation reaction and an addition polymerization reaction.

4. The method for prediction according to claim 2, wherein a number of elements in the intermediate layer is 1.1 times or more and less than 6 times a number of the explanatory factors.

5. The method for prediction according to claim 2, wherein a numerical value range of the explanatory factors input to the input layer is 0 or more and 1 or less, and a numerical value range of the objective factor output from the output layer is 0.2 or more and 0.8 or less.

6. The method for prediction according to claim 1, wherein the prediction target includes a polycondensation reaction and an addition polymerization reaction.

7. The method for prediction according to claim 1, wherein a number of elements in the intermediate layer is 1.1 times or more and less than 6 times a number of the explanatory factors.

8. The method for prediction according to claim 1 , wherein a numerical value range of the explanatory factors input to the input layer is 0 or more and 1 or less, and a numerical value range of the objective factor output from the output layer is 0.2 or more and 0.8 or less.

9. An information processing device comprising:

a processor that trains a neural network model based on actual data on a prediction target, and predicts an objective factor related to the prediction target based on explanatory factors related to the prediction target by the neural network model, and the neural network model comprises an input layer, an intermediate layer, and an output layer, and a coefficient of an activation function of the intermediate layer is larger than a coefficient of an activation function of the output layer.

10. A non-transitory computer-readable recording medium storing instructions executed by an information processing device that comprises a processor, the instructions causing the processor to execute:

training a neural network model based on actual data on a prediction target; and predicting an objective factor related to the prediction target based on explanatory factors related to the prediction target by the neural network model, wherein the neural network model comprises an input layer, an intermediate layer, and an output layer, and a coefficient of an activation function of the intermediate layer is larger than a coefficient of an activation function of the output layer.

* * * * *